US007521189B2

(12) United States Patent
Engelhard

(10) Patent No.: US 7,521,189 B2
(45) Date of Patent: Apr. 21, 2009

(54) DEVICES FOR GENERATING DETECTABLE POLYMERS

(75) Inventor: Eric K. Engelhard, Davis, CA (US)

(73) Assignee: Fair Isaac Corporation, Minneapolis, MN (US)

( * ) Notice: Subject to any disclaimer, the term of this patent is extended or adjusted under 35 U.S.C. 154(b) by 0 days.

(21) Appl. No.: 11/549,008

(22) Filed: Oct. 12, 2006

(65) Prior Publication Data

US 2008/0090232 A1   Apr. 17, 2008

(51) Int. Cl.
  C12Q 1/68 (2006.01)
  C12P 19/34 (2006.01)
  C12M 1/00 (2006.01)
(52) U.S. Cl. .................. 435/6; 435/91.2; 435/287.2
(58) Field of Classification Search ................ None
  See application file for complete search history.

(56) References Cited

U.S. PATENT DOCUMENTS

| 6,875,619 | B2 * | 4/2005 | Blackburn ................ 436/514 |
| 2004/0043479 | A1 * | 3/2004 | Briscoe et al. ........... 435/288.5 |
| 2005/0202414 | A1 | 9/2005 | Jia et al. |
| 2006/0177849 | A1 | 8/2006 | Oh et al. |
| 2006/0188917 | A1 | 8/2006 | Woudenberg et al. |

FOREIGN PATENT DOCUMENTS

WO    WO 02/01180    *  1/2002

OTHER PUBLICATIONS

Boivin et al., "Multiplex Real-Time PCR Assay for Detection of Influenza and Human Respiratory Syncytial Viruses," J. Clin. Microbiol., 2004, vol. 42, No. 1, pp. 45-51.*
Mazzulli et al., "Molecular Characterization of Nosocomial Outbreak of Human Repiratory Syncytial Virus on an Adult Leukemia/Lymphoma Ward," J.Infect.Diseases, 1999, vol. 180, pp. 1686-1689.*
Wittwer et al., "The LightCycler: A Microvolume Multisample Fluorimeter with Rapid Temperature Control," Biotechniques, 1997, vol. 22, pp. 176-181.*
Kuypers et al., "Evaluation of quantitative and type-specific real-time RT-PCR assays for the detection of respiratory syncytial virus in respiratory specimens from children," J.Clinical Virol., 2004, vol .31, pp. 123-129.*
Applied Biosystems, "Applied Biosystems Introduces the ABI Prism 7000 Sequence Detection System for Real-Time PCR Applications," Online publication (http://press.appliedbiosystems.com/corpcomm/applerapress.nsf/ABIDisplayPress/27597F200D0958B588256C140066EC9D?OpenDocument&type=abi), 2001, p. 1-2.*
Ko et al., "Rapid detection of infectious adenoviruses by mRNA real-time RT-PCR," J.Virol.methods, Aug. 2005, vol. 127, pp. 148-153, as evidenced by Cepheid, "SmartSystem: SmartCycler," product brochure, Jun. 2005, pp. 1-6.*

Richards et al., "A SYBR green, real-time RT-PCR method to detect and quantitate Norwalk virus in stools," J. Virol. Methods, 2004, vol. 116, pp. 63-70.*
Wu et al., "Development of Taqman RT-nested PCR system for clinical SARS-CoV detection," J. Virol. Methods, 2004, vol. 119, pp. 17-23.*
Payungpron, et al., "Single step multiplex real-time RT-PCR for H5N1 Influenza A virus detection," J. Virol. Methods, Jan. 2006, vol. 131, pp. 143.*
Kraft et al., "Evaluation of PCR Testing of Ethanol-Fixed Nasal Swab Specimens as an Augmented Surveillance Strategy for Influenza Virus and Adenovirus Identification," J. Clin.Microbiol., Apr. 2005, vol. 43, No. 4, pp. 1768-1775.*
Leamon et al., "A massively parallel PicoTiterPlate based Platform for discrete picoliter-scale polymerase chain reactions," Electrophoresis, 2003, vol. 24, pp. 3769-3777.*
Genbank Accession No. AY343597, referenced as 37790463, dated Apr. 13, 2004, p. 1-2.*
GenBank Accession No. AF510227, referenced as 21929761, dated Sep. 11, 2002, 2 pages.
GenBank Accession No. AF510235, referenced as 21929777, dated Sep. 11, 2002, 2 pages.
GenBank Accession No. AF510236, referenced as 21929779, dated Sep. 11, 2002, 2 pages.
GenBank Accession No. AF510287, referenced as 21929881, dated Sep. 11, 2002, 2 pages.
GenBank Accession No. AF512538, referenced as 21729393, dated Nov. 21, 2003, 3 pages.
GenBank Accession No. AF516119, referenced as 45386490, dated Mar. 12, 2004, 2 pages.
GenBank Accession No. AY114150, referenced as 21689580, dated Nov. 21, 2003, 3 pages.
GenBank Accession No. AY343549, referenced as 37790367, dated Apr. 13, 2004, 2 pages.
GenBank Accession No. AY343607, referenced as 37790483, dated Apr. 13, 2004, 2 pages.
GenBank Accession No. AY343609, referenced as 37790487, dated Apr. 13, 2004, 2 pages.
GenBank Accession No. AY343657, referenced as 37790583, dated Apr. 13, 2004, 2 pages.
GenBank Accession No. AY728167, referenced as 52352474, dated Sep. 25, 2004, 2 pages.
GenBank Accession No. AY728170, referenced as 52352480, dated Sep. 25, 2004, 2 pages.

(Continued)

Primary Examiner—Kenneth R. Horlick
Assistant Examiner—Molly E Baughman
(74) Attorney, Agent, or Firm—Fish & Richardson P.C.

(57) ABSTRACT

This document provides systems, devices, and methods involved in generating detectable polymers. For example, diagnostic systems, diagnostic devices, primer systems, and collections of primer systems are provided.

17 Claims, 1 Drawing Sheet

OTHER PUBLICATIONS

GenBank Accession No. AY927377, referenced as 61373253, dated Dec. 9, 2005, 2 pages.

GenBank Accession No. Z33411, referenced as 485873, dated May 10, 1994, 2 pages.

Beaucage and Caruthers, "Deoxynucleoside Phosphoramidites—A New Class of Key Intermediates for Deoxpolynucleotide Synthesis," *Tetrahedron Lett.*, 1981, 22:1859-1862.

Beuret, "Simultaneous detection of enteric viruses by multiplex real-time RT-PCR," *J. Virol. Meth.*, 2004, 115:1-8.

* cited by examiner

SEQUENCE LISTING

<160> NUMBER OF SEQ ID NOS: 20

<210> SEQ ID NO 1
<211> LENGTH: 25
<212> TYPE: DNA
<213> ORGANISM: respiratory syncytial viruses

<400> SEQUENCE: 1
aaaaacacaa caacaaccca aatac                           25

<210> SEQ ID NO 2
<211> LENGTH: 25
<212> TYPE: DNA
<213> ORGANISM: respiratory syncytial viruses

<400> SEQUENCE: 2
ttgaacactt caaagtgaaa atcat                           25

<210> SEQ ID NO 3
<211> LENGTH: 25
<212> TYPE: DNA
<213> ORGANISM: respiratory syncytial viruses

<400> SEQUENCE: 3
caaagttgaa cacttcaaag tgaaa                           25

-continued

```
<210> SEQ ID NO 4
<211> LENGTH: 24
<212> TYPE: DNA
<213> ORGANISM: respiratory syncytial viruses

<400> SEQUENCE: 4
aaaaacacaa caacaaccca aata                                          24

<210> SEQ ID NO 5
<211> LENGTH: 629
<212> TYPE: DNA
<213> ORGANISM: respiratory syncytial viruses

<400> SEQUENCE: 5
acctgaccca gaatccccag cttggaatca gcttcttcaa tctgtctgga actacatcac     60
aaaccaccgc catactagct ttaacaacac caagtgtcga gtcaatcctg caatctacaa    120
cagtcaagac caaaaacaca acaacaaccc aaatacaacc cagcaagccc accacaaaac    180
aacgccaaca caaaccacca aacaacccca atgatgattt tcactttgaa gtgttcaact    240
ttgtaccctg cagcatatgc agcaacaatc caacttgctg ggccatctgc aaaagaatac    300
caagcaaaaa acctggaaag aaaaccacca ccaagcccac gaaaaaacca accatcaaga    360
caaccaaaaa agatctcaaa cctcaaacca caaaaccaaa ggaagcacct actaccaagc    420
ccacagaaaa gccaaccatc aacatcacca aaccaaacat cagaactaca ctgctcacca    480
acagtaccac aggaaatcta gaacacacaa gtcaagagga aaccctccat tcaacctcct    540
ccgaaggcaa tacaagccct tcacaaatct atacaacatc cgagtaccta tcacaacctc    600
catctccatc caacataaca gaccagtag                                     629

<210> SEQ ID NO 6
<211> LENGTH: 923
<212> TYPE: DNA
<213> ORGANISM: respiratory syncytial viruses

<400> SEQUENCE: 6
ggggcaaatg caaacatgtc caaaaacaag gaccaacgca ccgctaagac actagaaaag     60
acctgggaca ctctcaatca tctattattc atatcatcgt gcttatacaa gttaaatctt    120
aaatctatag cacaaatcac attatccatt ctggcaatga taatctcaac ttcacttata    180
attgcagcca tcatattcat agcctcagca aacaacaaag tcacactaac aactgcaatc    240
atacaagatg caacaaacca gatcaagaac acaaccccaa catacctgac ccagaatccc    300
cagcttggaa tcagcttctt caatctgtct ggaactacat cacaaaccac cgccatacta    360
gctttaacaa caccaagtgt cgagtcaatt ctgcaatcta caacagtcaa gaccaaaaac    420
acaacaacaa cccaaataca acccagcaag cccaccacaa aacaacacca aaacaaacca    480
ccaaacaaac ccaataatga ttttcacttt gaagtgttca actttgtacc ctgcagcata    540
tgcagcaaca atccaacttg ctgggccatc tgcaaaagaa taccaagcaa aaaacctgga    600
aagaaaacca ccaccaagcc cacaaaaaaa ccaaccatca agacaaccaa aaaagatctc    660
aaacctcaaa ccacaagacc caagggagca tctaccacca agcccacaga aaagccaacc    720
atcaacatca ccaaaccaaa catcagaact acactgctca ccaacagtac cacaggaaat    780
ctagaacaca caagtcaaga ggaaaccctc cattcaacct cctctgaagg caatacaagc    840
tctccacaag tctatacaac atccgagtac ctatcacaac ctccatctcc atccaacata    900
acaaaccagt agtcattaaa aaa                                           923
```

```
<210> SEQ ID NO 7
<211> LENGTH: 629
<212> TYPE: DNA
<213> ORGANISM: respiratory syncytial viruses

<400> SEQUENCE: 7
acctcaccca gaatcccag cttggaatca gcttctccaa tctgtccgaa actacatcgc      60
aacccaccac catactggct tcaacaacac caagtgctga gtcaacccca caatccacaa    120
cagtcaagat caaaaacaca caacaaccc aaatacaacc tagcaaaccc accacaaaac    180
aacgccaaaa caaccacaa aacaaaccca ataatgattt cactttgaa gtgttcaatt     240 ttgtaccctg cagcatatgc agcaacaatc caacctgctg ggccatctgc aaaagaatac    300
caaacaaaaa acctggaaag aaaaccacca ccaagcccac aaaaaaacca accatcaaga    360
caaccaaaaa agatcccaaa cctcaaacca caaaaccaaa ggaagcactc actaccaagc    420
tcacagaaaa gccaaccatc aacaccacca aaacaaacat cagaactaca ctgctcacct    480
ccaacaccac aggaaatcca gaacacacaa gccaaaagga acccctccac tcaaccacct    540
ccgaaggcaa tccaagcctt tcacaagtct atacaacatc cgagtaccta tcacaatctc    600
catctccatc caacacaaca aaatggtag                                     629

<210> SEQ ID NO 8
<211> LENGTH: 922
<212> TYPE: DNA
<213> ORGANISM: respiratory syncytial viruses

<400> SEQUENCE: 8
ggggcaaatg caaacatgtc caaaaccaag gatcaacgca ccgccaagac actagaaagg     60
acctgggaca ctcttaatca tctattattc atatcatcgt gcttatacaa gttaaatctt    120
aaatctatag cacaaatcac attatccatt ttggcaatga atctcaac ttcacttata     180 attgcagcca tcatattcat agcctcagca aaccacaaag tcacaccaac aactgcaatc    240
acacaagatg caacaagcca gatcaagaac acaaccccaa catacctcac ccagaatccc    300
cagcttggaa tcagcttctc taatctgtcc gaaaccacat cacaacctac caccacacca    360
gctctaacaa caccagtgc tgagtcaacc ccacaatcca caacagtcaa gaccaaaaac    420
acaacaacaa cccaaataca aaccagcaag cccaccacaa acaacgccaa aacaaaccca    480
ccaaacaaac ccaacaatga ttttcacttt gaagtgttca actttgtacc ctgcagcata    540
tgcagcaaca atccaacctg ctgggctatc tgcaaaagaa taccaaacaa aaaacctgga    600
aagaaaacca ccaccaagcc cacaaaaaaa ccaaccatca agacaaccaa aaagatttc    660 aaacctcaaa ccacaaaacc aaaggaagta cttaccacca gcccacaga aaagccaacc    720 atcaacacta ccaaaacaaa catcaaaact acactgctca ccaccaacac cacaggaaat    780
ccagaacaca caagtcaaaa ggaaacctc cactcaacct ccccgaagg caatccaagc    840 ccttcacaag tctatacaac atctgagtac ccatcacaac ctccatctcc atccaacaca    900
acagactagt agtcatttaa aa                                           922

<210> SEQ ID NO 9
<211> LENGTH: 600
<212> TYPE: DNA
<213> ORGANISM: respiratory syncytial viruses

<400> SEQUENCE: 9
tgcaacaagc cagatcaaga acacaacccc aacatacctc acccagaatc cccagcttgg     60
```

-continued

```
aatcagcttc tccaatctgt ctgaaaccac atcacaaccc accaccacac cagctctagc      120
aacaccaagt gctgagtcaa ccctacaatc tacaatagtc aagaccaaaa acacaacaac      180
aacccaaata caacccagca agccaccac aaaacaacgc caaaacaaac caccaaataa       240
acccaacaat gattttcact ttgaagtgtt caactttgta ccctgcagca tatgcagcaa      300
caatccaacc tgctgggcta tctgcaaaag aataccaaac aaaaaacctg gaaagaaaac     360
caccaccaag cccacaaaaa aaccaactat caagacaacc aaaaaagatc tcaaacctca      420
aaccacaaaa ccaaaggaag tacttaccac caagcccaca gaaaagccaa ctatcaacac     480
caccagaaca aacatcggaa ctacactgct caccaccaat accacaggaa atccagaata    540
cacaagtcaa aaggaaaccc ttcactcaac ctcccccgaa ggcaatccaa gcccttcaca    600
```

<210> SEQ ID NO 10
<211> LENGTH: 1122
<212> TYPE: DNA
<213> ORGANISM: respiratory syncytial viruses

<400> SEQUENCE: 10

```
aaaccacatc aacatctcac catgcaagcc atcatctata ccataaagta gttaattaaa     60
aatagtcata caatgaact aagatattaa gaccaacaac aacgttgggg caaatgcaaa     120
catgtccaaa accaaggacc aacgcaccgc caagacacta gaaaggacct gggacactct    180
taatcatcta ttattcatat catcgtgctt atacaagtta atcttaaat ctatagcaca     240 aatcacatta tctattttgg caatgataat ctcaacttca cttataattg cagccatcat    300
attcatagcc tcggcaaacc acaaagtcac actaacaact gcaatcatac aagatgcaac    360
aaaccagatc aagaacacaa ccccaacata cctcacccag aatccccagc ttggaatcag    420
cttctccaat ctgtccgaag ccacatcaca acccaccacc atactagctt caacaacacc    480
aaatgtcgag tcaaccccac aatccacaac agtcaagacc aaaaacacaa caacaaccca    540
aatacaacct agcaagtcca ccacaaaaca cgtcaaaac aaaccacaaa acaaacccaa     600
taatgatttt cactttgaag tgttcaactt tgtaccctgc agcatatgca gcaacaatcc    660
aacttgctgg gctatctgca aaagaatacc aaacaaaaaa cctggaaaga aaccaccac    720 caagcccaca aaaaaccaa ccaccaagac aaccaaaaaa gatctcaaac ctcaaaccac    780 aaaccaaag gaagtactta ccaccaagcc caagaaaag caaaccatca acaccaccaa    840
aacaaacatt agaaccacac tgctcacctc caacaccaca ggaaatccag aacacacaag    900
ccaaaaggaa accctccact caaccacctc cgaaggcaat ccaagccctt cacaagtcta    960
tacaacatcc gagtacccat cacaatctct atctccatcc aacacaacat actattagtc   1020
attaaaaagt gtattattgc aaaaagccat aaccaaatca aacagaatca aaatcaactg   1080
tggggcaaat aacaatggag ttgccaatcc tcaaagcaaa tg                      1122
```

<210> SEQ ID NO 11
<211> LENGTH: 508
<212> TYPE: DNA
<213> ORGANISM: respiratory syncytial viruses

<400> SEQUENCE: 11

```
tgcaacaagc cagatcaaga acacaacccc aacatacctc acccagaatc cccagcttgg     60
aatcagcttc tccaatctgt ctgaaaccac atcacaaccc accaccacac cagctctagc   120
aacaccaagt gctgagtcaa ccccacaatc cacaacagta aagaccaaaa acacaacaac   180
```

-continued

```
aacccaaata caacccagca agcccaccac aaaacaacgc caaaacaaac caccaaataa    240
acccaacaat gattttcact ttgaagtgtt caactttgta ccctgcagca tatgcagcaa    300
caatccaacc tgctgggcta tctgcaaaag aataccaaac aaaaaacctg gaaagaaaac    360
caccaccaag cccacaaaaa aaccaactat caatacaacc aaaaaagatc tcaaacctca    420
aaccacaaaa ccaaaggaag tacttaccac caagcccaca gaaaagccaa ctatcaatac    480
caccagaaca aacatcggaa ctacactg                                       508

<210> SEQ ID NO 12
<211> LENGTH: 464
<212> TYPE: DNA
<213> ORGANISM: respiratory syncytial viruses

<400> SEQUENCE: 12
tgcaacaaac cagatcaaga acacaacccc aacatacctc acccagaatc cccagcttgg     60
aatcagcttc tccaatctgt ccgaaactac atcacaaccc accaccatac tagcttcaac    120
aacaccaagt gctgagtcaa ccccacaatc cacaacagtc aagatcaaaa acacaacaac    180
aacccaaata caacctagca agcccaccac aaaacaacgc caaaacaaac cacaaaacaa    240
acccaataat gattttcact ttgaagtgtt caactttgta ccctgcagca tatgcagcaa    300
caatccaact tgctgggcta tctgcaaaag aataccaaac aaaaaacctg gaaagaaaac    360
caccaccaag cccacaagaa aaccaaccat caagacaacc aaaaaagatc tcaaacctca    420
aaccacaaaa ccaaaggaag tacttaccac caggcccaca gaaa                     464

<210> SEQ ID NO 13
<211> LENGTH: 1177
<212> TYPE: DNA
<213> ORGANISM: respiratory syncytial viruses

<400> SEQUENCE: 13
gatagctcaa acagtaacct tgcatttgta agtgaactac cctcacctct tcacaaaacc     60
acatcaacat ctcaccatgc aagccatcat ctataccata aagtagttaa ttaaaaatag    120
tcataacaat gaactaggat attaagacca aaaacaacgt tggggcaaat gcaaacatgt    180
ccaaaaccaa ggaccaacgc accgccaaga cattagaaag gacctgggac actctcaatc    240
atctattatt catatcatcg tgcttataca agttaaatct taaatctata gcacaaatca    300
cattatctat tttggcaatg ataatctcaa cttcacttat aattgcagcc atcatattca    360
tagcctcggc aaacaacaaa gtcacactaa caactgcaat catacaagat gcaacaaacc    420
agatcaagaa cacaacccca acatacctca cccagaatcc ccagcttgga atcagcttct    480
ccaatctgtc cggaactaca tcacaatcca ccaccatact agcttcaaca acaccaagtg    540
ctgagtcaac cccacaatcc acaacagtca agatcaaaaa cacaacaaca acccaaatac    600
aacctagcaa atccaccaca aaacaacgcc aaaacaaacc acaaaacaaa cccaacaatg    660
attttcactt tgaagtgttc aattttgtac cctgcagcat atgcagcaac aatccaacct    720
gctgggccat ctgcaagaga ataccaaaca aaaaacctgg aaagaaaacc accaccaagc    780
ccacaaaaaa accaaccatc aagacaacca aaaaagatcc caaacctcaa accacaaaac    840
caaaggaagt actcaccacc aagcccacag aaaagccaac catcgacacc accaaaacaa    900
acatcagaac tacactgctc acctccaaca ctacaggaaa tccagaacac acaagtcaag    960
aggaaaccct ccactcaacc acctccgaag gcaatctaag cccatcacaa gtctatacaa   1020
catccgagta cctatcacaa tctccatctt catctaacac aacaaaatga tagtcattaa   1080
```

```
aaagcgtatt gttgcaaaaa gccatgacca aatcaaacag aatcaaaatc aactctgggg    1140
caaataacaa tggagttgcc aatcctcaat aacaaat                             1177

<210> SEQ ID NO 14
<211> LENGTH: 629
<212> TYPE: DNA
<213> ORGANISM: respiratory syncytial viruses

<400> SEQUENCE: 14
acctgactca gaatcccag cttggaatca gcttctccaa tctgtctgaa actacatcac      60
aaaccaccac catactagct tcaacaacac caagtgtcga gtcaaccctg caatccacaa    120
cagtcaagac caaaaacaca acaacaaccc aaatacaacc cagcaaaccc accacaaaac    180
aacgccaaaa caaaccacca aacaaaccca ataatgattt cactttgaa gtgttcaact     240 ttgtaccttg cagcatatgc agcaataatc caacctgctg ggctatctgt aaaagaatac    300
caaacaaaaa acctgggaag aaaaccacca ccaagcccac aaaaaaacca accatcaaga    360
caaccaaaaa agatctcaaa cctcaaacca caaaaccaaa ggaagcacct accaccaagc    420
ctacagaaaa gccaaccatc aacaccacca aaacaaacat cagaactaca ctgctcacca    480
acagtaccac aggaaattta gaacacacaa gtcaagagga accctccac tcaacctcct    540 ccgaaggcaa tccaagccct tcacaagtct atacaacatc tgagtaccca tcacaacctc    600
catctccatc caacacaaca aaccagtag                                      629

<210> SEQ ID NO 15
<211> LENGTH: 629
<212> TYPE: DNA
<213> ORGANISM: respiratory syncytial viruses

<400> SEQUENCE: 15
tcctcaccca gaatcccag tttggaatca gcttctccaa tctgtccgaa actacatcac      60
aaatcaccac catactagct tcaacaacac caagtatcga atcaaccctg ctatccacaa    120
cagtcaagac caaaaacaca acaacaaccc aaatacaacc cagcaagccc accacaaaac    180
aacgccacaa caaccacca aacaaaccca acaatgattt cactttgaa gtgttcaact      240 ttgtaccttg cagcatatgc agcaacaatc caacctgctg ggctatctgt aaaagaatac    300
caaacaaaaa acctggaaag aaaaccacca ccaagcccac aaaaaaacca accaccagga    360
caaccaaaaa agatctcaaa cctcaaacca caaaaccaaa ggaaacactc accaccaagc    420
ccacagaaaa gtcaaccatc aacaccacca aaacaaacat cagaactaca atgcttatca    480
acaataccac aggaaatcca gaaaacacaa gtcaacagga accctccac tcaacctcct    540 ccgagggcaa tccaagccct tcacaagtct atacaacatc cgagtaccca tcacaacctc    600
catctccgtt caacacaaca gcctagtag                                      629

<210> SEQ ID NO 16
<211> LENGTH: 390
<212> TYPE: DNA
<213> ORGANISM: respiratory syncytial viruses

<400> SEQUENCE: 16
tgcaacaaac cagatcaaga acacaacccc aacatacctc acccagaatc cccagcttgg     60
aatcagcttc tccaatctgt ccgaaactac atcacaaccc accatac tagcttcaac       120 aacaccaagt gctgagtcaa ccccacaatc cacaacagtc aagatcaaaa acacaacaac    180
```

-continued

```
aacccaaata caacctagca agcccaccac aaaacaacgc caaaacaaac cacaaaacaa    240
acccaataat gattttcact ttgaagtgtt caactttgta ccctgcagca tatgcagcaa    300
caatccaact tgctgggcta tctgcaaaag aataccaaac aaaaaacctg gaaagaaaac    360
caccaccaag cccacaagaa aaccaaccat                                     390
```

<210> SEQ ID NO 17
<211> LENGTH: 277
<212> TYPE: DNA
<213> ORGANISM: respiratory syncytial viruses

<400> SEQUENCE: 17

```
acacaaccct aacatacctg acccagaatc cccagcttgg aatcagcttc ttcaatctgt     60
ctggaactac atcacaaacc accgccatac tagatttaac aacaccaagt gtcgagtcaa    120
tcctgcaatc tacaacagtc aagaccaaaa acacaacaac aacccaaata caacccagca    180
agcccaccac aaaacaacgc aaaaacaaac caccaaacaa acccaatgat gattttcact    240
ttgaagtgtt caactttgta ccctgcagca tatgcaa                             277
```

<210> SEQ ID NO 18
<211> LENGTH: 629
<212> TYPE: DNA
<213> ORGANISM: respiratory syncytial viruses

<400> SEQUENCE: 18

```
acctcaccca gaatccccag cttggaatca gcttctccaa tctgtccgaa actacatcac     60
aacccaccac catactagct tcaacaacac caagtgctga gtcaacccca caatccacaa    120
cagtcaagat caaaaacaca acaacaaccc aaatacaacc tagcaaaccc accacaaaac    180
aacgccaaaa caaaccacaa aacaaaccca ataatgattt tcactttgaa gtgttcaact    240
ttgtaccctg cagcatatgc agcaacaatc caacctgctg ggccatctgc aaaagaatac    300
caaacaaaaa acctggaaag aaaaccacca ccaagcccac aaaaaaacca accatcaaga    360
caaccaaaaa agatcccaaa cctcaaacca caaaaccaaa ggaagtactc accaccaagc    420
ccacagaaaa gccaaccatc aacaccacca aaacaaacat cagaactaca ctgctcacct    480
ccaacaccac aggaaatcca gaacacacaa gtcaaaagga aaccctccac tcaaccacct    540
ctgaaggcaa tctaagccct tcacaagtct atacaacatc cgagtaccta tcacaatctc    600
tatctccatc caacacaaca aaatggtag                                      629
```

<210> SEQ ID NO 19
<211> LENGTH: 3332
<212> TYPE: DNA
<213> ORGANISM: respiratory syncytial viruses

<400> SEQUENCE: 19

```
ggggcaaata atcatcggag gaaatccaac caatcacaat atctgtcaac atagaccagt     60
caacacgcca aacaaaacaa accaatggaa aatacatcca taacaataga attctcaagc    120
aaattctggc cttactttac actaatacat atgatcacaa caataatctc tttgctaatc    180
ataatctcca tcatgattgc aatactaaac aaactctgtg aatataacgt attccataac    240
aaaacctttg agctaccaag agctcgagtc aatacatagc attcaccaat ctgatggctc    300
aaaacagtaa ccttgcattt gtaagtgaac aatcttcacc tttctacaaa atcacatcaa    360
catctcacca tgcaagccat catccatact ataaagtagt taattaaaaa tagttataac    420
aatgaactaa gatattaaga ctaacaacaa cgttggggca aatgcaaaca tgtccaaaac    480
```

-continued

```
caaggaccaa cgcaccgcca agacactgga aaagacctgg gacactctca atcatctatt    540
attcatatca tcgtgcttat acaagttaaa tcttaaatct atagcacaaa tcacattatc    600
cattctggca atgataatct caacttcact tataattgta gctatcatat tcatagcctc    660
agcaaacaac aaagtcacac taacaactgc aatcatacaa gatgcaacaa gccagatcaa    720
gaacacaacc ccaacatacc tgacccagaa tccccagctt ggaatcagct tcttcaatct    780
gtctggaact atatcacaaa ccaccgccat actagctcca acaacaccaa gtgtcgagcc    840
aatcctgcaa tctacaacag tcaagaccaa aaacacaaca caacccaaa tacaacccag    900 caagctcacc acaaaacaac gccaaaacaa accaccaaac aaacccaatg atgattttca    960
ctttgaagtg ttcaactttg taccctgcag catatgcagc aacaatccaa cttgctgggc   1020
catctgcaaa agaataccaa gcaaaaaacc tggaaagaaa accaccacca agcccacgaa   1080
aaaacaaacc atcaagacaa ccaaaaaaga tctcaaacct caaccacaa aaccaaagga   1140 agcacctacc accaagccca cagaaaagcc aaccatcaac atcaccaaac caaacatcag   1200
aactacactg ctcaccaaca gtaccacagg aaatctagaa cacacaagtc aagaggaaac   1260
cctccattca acctcctccg aaggcaatac aagcccttca caaatctata caacatccga   1320
gtacctatca caacctccat ctccatccaa cataacagac cagtagtcat aaaaagcgt   1380 attattgcaa aaaccatga ccaaatcaaa cagaatcaaa ataagctctg ggcaaataa   1440 caatggattt gccaatcctc aaaacaaatg caattaccac aatccttgct gcagtctcac   1500
tctgtttcgc ttccagtcaa aacatcactg aagaatttta tcaatcaaca tgcagtgcag   1560
ttagcaaagg ctatcttagt gctttaagaa ctggttggta tactagtgtt ataactatag   1620
aattaagtaa tatcaaggaa aataagtgta atggaacaga cgctaaggta aaattgataa   1680
aacaagaatt agataaatat aaaaatgctg taacagaatt gcagttgctc atgcaaagca   1740
caccagcagc caacaatcga gccagaagag aactaccaag gtttatgaat tatacactca   1800
acaataccaa aaataacaat gtaacattaa gcaagaaaag gaaagaaga tttcttggct   1860 tttttgttagg tgttggatct gcaatcgcca gtggcattgc tgtatctaaa gtcctgcacc   1920
tagaagggga agtgaacaaa atcaaaagtg ctctactatc cacaaacaag gctgtagtca   1980
gcttatcaaa tggagttagt gtcttaacca gcaaagtgtt agacctcaaa aactatatag   2040
ataaacagtt gttacccatt gtgaacaagc aaagctgcag catatcaaac attgaaactg   2100
tgatagaatt ccaacaaaag aacaacagac tactagagat taccagggaa tttagtgtta   2160
atgcaggtgt aactacacct gtaagcactt atatgttaac aaatagtgaa ttattatcat   2220
taatcaatga tatgcctata acaaatgatc agaaaaagtt aatgtccaac aatgttcaaa   2280
tagttagaca gcaaagttac tctatcatgt ccataataaa ggaggaagtc ttagcatatg   2340
tagtacaatt accactatat ggtgtaatag atacaccttg ttggaaacta cacacatccc   2400
ctctatgcac aaccaacaca aaggaagggt ccaatatctg tttaacaaga accgacagag   2460
gatggtactg tgacaatgca ggatcagttt ctttcttccc acaagctgaa acatgcaaag   2520
ttcaatcgaa tcgagtattt tgtgacacaa tgaacagttt aacattacca agtgaagtaa   2580
atctctgcaa cattgacata ttcaacccta aatatgattg caaaattatg acttcaaaaa   2640
cagatgtaag cagctccgtt atcacatctc taggagccat tgtgtcatgc tatggcaaaa   2700
ctaaatgtac agcatccaat aaaaatcgtg gaatcataaa gacatttct aacgggtgtg   2760 attatgtatc aaataagggg gtggacactg tatctgtagg taatacatta tattatgtaa   2820
```

-continued

| | |
|---|---|
| ataagcaaga aggaaaaagt ctctatgtaa aaggtgaacc aataataaat ttctatgacc | 2880 |
| cattagtgtt cccttctgat gaatttgacg catcaatatc tcaagtcaat gagaagatta | 2940 |
| accagagcct agcatttatt cgtaaatccg atgaattatt acataatgta aatgttggta | 3000 |
| aatccaccac aaatatcatg ataactacta taattatagt gattatagta atattgttat | 3060 |
| tattaattgc agttgggctg ttcctatact gcaaggccag aagcacacca gtcacactaa | 3120 |
| gcaaggatca actgagtggt ataaataata ttgcatttag taactgaata aaaatagtac | 3180 |
| ctaatcatgt tcttacaatg gttcaccatc cgaccataga cgacccatct atcattggat | 3240 |
| tttcttaaag tctgaacttc atcgcaactc tcatctataa accatctcac ttacactatt | 3300 |
| taagtagatt cctattttat agttatataa aa | 3332 |

<210> SEQ ID NO 20
<211> LENGTH: 3332
<212> TYPE: DNA
<213> ORGANISM: respiratory syncytial viruses

<400> SEQUENCE: 20

| | |
|---|---|
| ggggcaaata atcattaagg gaaatccaac taatcacaac atctgtcaac atagacaagt | 60 |
| caacacgtta gacaaaatca accaatggaa aatacatcca taacaataga attctcaagc | 120 |
| aaattctggc cttactttac actaatacac atgataacaa caataatctc tttgctaatc | 180 |
| ataatctcca tcatgattgc aatactaaac aaactctgcg aatataatgc atttcataac | 240 |
| aaaacctttg agctaccaag agctcgaatc aatacatagc attcactaat ctgatggctc | 300 |
| aaaacagcaa ccttgcattt gtaagtgaac taccctcacc tcttcacaaa accacatcaa | 360 |
| catctcacca tacaagccat catctatacc ataaagtagt taattaaaaa tagtcataac | 420 |
| aatgaactac gatattaaga tcaacaacaa cgttggggca aatgcaaaca tgtccaaaac | 480 |
| caaggaccaa cgcaccgcca agacactaga aaggacctgg gacactctta atcatctatt | 540 |
| attcatatca tcgtgcttat acaagttaaa tcttaaatct atagcacaaa tcacattatc | 600 |
| tattttggca atgataatct caacttcact tataattgca gccatcatat tcatagcctc | 660 |
| ggcaaaccac aaagtcacac taacaactgc aatcatacaa gatgcaacaa accagatcaa | 720 |
| gaacacaacc ccaacatacc tcacccagaa tccccagctt ggaatcagct tctccaatct | 780 |
| gtccgaaact acatcacaac ccatcaccat actagcttca acaacaccaa gtgctgagtc | 840 |
| aaccccacaa tccacaacag tcaagaccaa aacacaacaa caacccaaa tacaacctag | 900 |
| caagtccacc acaaaacaac gccaaaacaa accacaaaac aaacccaata tgatttttca | 960 |
| ctttgaagtg ttcaactttg taccttgcag catatgcagc aacaatccaa cttgctgggc | 1020 |
| tatatgcaaa agaataccaa acaaaaaacc tggaaagaaa accaccacca agcccacaaa | 1080 |
| aaaaccaacc atcaagacaa ccaaaaaaga tctcaaacct caaccacaa atcaaaggaa | 1140 |
| agtacttacc accaagccca cagaaaagcc aaccatcaac accaccaaaa caaacatcag | 1200 |
| aactacactg ctcatctcca acaccacagg aaatccagaa cacacaagtc aaaaggaaac | 1260 |
| cctccactca accacctccg aaggcaatcc aagcccttca caagtctata caacatccga | 1320 |
| gtacctatca caatctctat ctccatccaa cacaacatac tattagtcat taaaaagtgt | 1380 |
| attattgcaa aaagccataa ccaaatcaaa cagaatcaaa atcaactctg ggcaaataa | 1440 |
| caatggagtt gccaatcctc aaagcaaatg ctattaccac aatccttgct gcagtcacac | 1500 |
| tctgttttgt ttccagtcaa aacatcactg aagaatttta tcaatcaaca tgcagtgcag | 1560 |
| ttagcaaagg ctatcttagt gctctaagaa ctggttggta tactagtgtt ataactatag | 1620 |

-continued

```
aattaagtaa tatcaaggaa aataagtgta atggaacaga tgctaaggta aaattgataa    1680
aacaagaatt agataaatac aaaaatgctg taacagaatt gcagttgctc atgcaaagca    1740
caccagcagc caacaatcga gccagaagag aattaccaag atttatgaat tatacactca    1800
acaataccaa aaacaccaat gtaacattaa gcaagaagag gaaagaaga tttcttggct     1860 ttttgttagg tgttggatct gcaatcgcca gtggcattgc cgtatccaag gtcctgcacc    1920
tagaagggga agtgaacaaa atcaaaagtg ctctactatc cacaaacaaa gctgtagtca    1980
gcttatcaaa tggagtcagt gtcttaacca gcaaagtgtt agatctcaaa aactatatag    2040
ataaacagtt gttacctatt gtgaacaagc aaagctgcag catatcaaac attgaaactg    2100
tgatagagtt ccaacaaaag aacaacagac tactagagat taccagagaa tttagtgtta    2160
atgcaggtgt aactacacct gtaagcactt atatgttaac taatagtgaa ttattatcat    2220
taatcaatga tatgcctata acaaatgatc agaaaaagtt aatgtccaac aatgttcaaa    2280
tagttagaca gcaaagttac tctatcatgt ccataataaa ggaggaagtc ctagcatatg    2340
tagtacaatt accactatat ggtgtaatag atacaccttg ttggaaactg cacacatccc    2400
ctctatgcac aaccaacaca aaggaagggt ccaacatctg cttaacaaga accgacagag    2460
gatggtactg tgacaatgca ggatcagtat ctttcttccc acaagctgaa acatgtaaag    2520
ttcaatcgaa tcgggtattt tgtgacacaa tgaacagttt aacattacca agtgaggtaa    2580
atctctgcaa cgttgacata ttcaacccca aatatgattg caaaattatg acttcaaaaa    2640
cagatgtaag cagctccgtt atcacatctc tgggagccat tgtgtcatgc tatggcaaaa    2700
ccaaatgtac agcatccaat aaaaatcgtg ggatcataaa gacattttct aacgggtgtg    2760
attatgtatc aaataagggg gtggatactg tgtctgtagg taatacatta tattatgtaa    2820
ataagcaaga aggcaaaaat ctctatgtaa aaggtgaacc aataataaat ttctatgacc    2880
cattagtgtt cccctctgat gaatttgatg catcaatatc tcaagtcaat gagaagatta    2940
accagagtct agcatttatt cgtaaatcag atgaattatt acataatgta aatgctggta    3000
aatccaccac aaatatcatg ataactacta taattatagt gattatagta atattgttat    3060
cattaattgc agttggactg cttctatact gcaaggccag aagcacacca gtcacactaa    3120
gtaaggatca actgagtggt ataaataata ttgcatttag tagctgaata aaaatagcat    3180
ctaatcatat tcttacaatg gttcactatc tgaccataga taacccatct atcattggat    3240
tctcttaaaa tttgaacttc atcacaactt tcatctataa accatctcac ttacactatt    3300
taagtagatt cctattttat agttatataa aa                                  3332
```

DEVICES FOR GENERATING DETECTABLE POLYMERS

BACKGROUND

1. Technical Field

This document relates to systems, devices, and methods involved in generating detectable polymers.

2. Background Information

Many different types of devices exist for generating polymers such as labeled deoxyribonucleic acids. For example, tubes, tube retainer trays, microtiter plates, microfluidic cards, and glass slides containing arrays have been fabricated to allow a user to generate polymers. The HT7900 Micro Fluidic Card™ is an example of a microfluidic card designed to allow a user to generate polymers. In this case, the microfluidic card functions as a structured array of reaction chambers and contains input ports for inserting samples into the card. The HT7900 Micro Fluidic Card™ is available from Applied Biosystems Group (Foster City, Calif.).

In addition, many different techniques have been developed to detect a generated polymer. For example, machines designed to read fluorescent signals from each well of a microtiter plate have been developed. The FLx800™ reader is an example of an absorbance and fluorescence instrument for measuring samples in various microplate arrangements. The reader can used in numerous fluorescence and absorbance applications in research and routine investigations. Its fluorescence filters are arranged in filter wheels. The reader can handle 6, 48, 96, and 384 well plates and can detect wavelengths in the fluorescence spectral range. Gen5™ data collection and analysis software can be used for data capture, and standard reads and data can be downloaded into Excel for further analysis. Dual optical channels can allow for measurements from above or below the plate. Light to and from the samples can be focused by a lens. The FLx800™ reader is available from BioTek Instruments, Inc. (Winooski, Vt.).

SUMMARY

This document relates to systems, devices, and methods involved in generating detectable polymers. For example, this document provides diagnostic systems, diagnostic devices, primer systems, and collections of primer systems. A diagnostic system can include a diagnostic device containing a collection of primer systems. This document also provides methods for making diagnostic systems, diagnostic devices, primer systems, and collections of primer systems. For example, this document provides methods for making a diagnostic device containing a collection of primer systems. The systems, devices, and methods provided herein can be used to generate detectable polymers such as amplified deoxyribonucleic acid molecules. In addition, the systems, devices, and methods provided herein can be used to detect respiratory syncytial viruses within samples. Detecting respiratory syncytial viruses can help clinicians provide important prognostic information to patients.

The description provided herein is based, in part, on the discovery of effective primer systems for generating detectable polymers. For example, a diagnostic device provided herein can contain primer systems effective to detect respiratory syncytial viruses within samples. Such a diagnostic device can be used to aid clinicians in assessing a patient's prognosis. The description provided herein also is based, in part, on the discovery of primer systems having the ability to not only amplify particular nucleic acid sequences from different respiratory syncytial viruses, but also to not amplify nucleic acid sequences from non-respiratory syncytial virus sources such as a human's genome. In addition, the description provided herein is based, in part, on the discovery of primer systems that can be used simultaneously with a collection of primer pairs under the same amplification reaction conditions to amplify different target nucleic acids if present in the sample being tested.

In general, one aspect of this document features a device comprising, or consisting essentially of, a housing having a plurality of locations, wherein each of the locations contains a primer system, wherein the primers of each primer system are between 18 and 28 nucleotides in length and have a theoretical melting temperature between 58° C. and 62° C., wherein the device comprises at least one primer system capable of producing an amplification product diagnostic for an respiratory syncytial virus, and wherein each amplification product, when produced, is between 100 and 400 nucleotides in length. Each of the locations can be a chamber. Each of the locations can be a well. The primers of each primer system can be between 23 and 27 nucleotides in length. The primers of each primer system can have a theoretical melting temperature between 59° C. and 61° C. The housing can comprise additional locations, wherein each of the additional locations contains a primer pair. At least one of the additional locations can comprise a primer pair capable of producing an amplification product from human nucleic acid. Each of the locations can comprise an intercalating dye, and wherein each amplification product, when produced, can be labeled with the intercalating dye. The intercalating dye can be a green fluorescent dye. The intercalating dye can be SYBR Green, LC Green, or SYTO9. Each amplification product, when produced, can be between 100 and 300 nucleotides in length.

In another aspect, this document features method for detecting an respiratory syncytial virus within a sample. The method comprises, or consists essentially of, (a) performing a nucleic acid amplification reaction using the sample as a source of template and a diagnostic device, wherein the device comprises a housing having a plurality of locations, wherein each of the locations contains a primer system, wherein the primers of each primer system are between 18 and 28 nucleotides in length and have a theoretical melting temperature between 58° C. and 62° C., wherein the device is capable of producing an amplification product diagnostic for an respiratory syncytial virus, and wherein each amplification product, when produced, is between 100 and 400 nucleotides in length, and (b) determining which locations of the device contain a primer system that resulted in the formation of amplification product, thereby detecting an respiratory syncytial virus. The sample can be a sample obtained from a human. The nucleic acid amplification reaction can comprise at least 10 cycles. The nucleic acid amplification reaction can comprise at least 20 cycles. The nucleic acid amplification reaction can comprise a denaturing step at about 94° C. or about 95° C. The nucleic acid amplification reaction can comprise an annealing step at about 60° C. The nucleic acid amplification reaction can comprise an extension step at about 72° C. The sample can be a mucus sample. The sample can be a sample obtained from the human using a swab. The sample can be a sample processed to obtain viral nucleic acid. Each of the locations can comprise an intercalating dye, wherein each amplification product, when produced, is labeled with the intercalating dye, and wherein determining which locations of the device contain a primer system that resulted in the formation of amplification product is based on a signal from the dye. The amplification reaction can be performed in a thermal cycler device configured to receive the diagnostic device. The determining step (b) can be performed in using a dye reader device configured to receive the diagnostic device. The amplification reaction and the determining step (b) can be performed in a machine configured to receive the diagnostic device, the machine comprising a thermal cycler device and a dye reader device. The machine can be capable of providing output indicating the presence of the respiratory syncytial virus. The machine can be capable of providing output indicating the primer system that detected the presence of the respiratory syncytial virus. The output can be a paper printout or a computer readable file.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
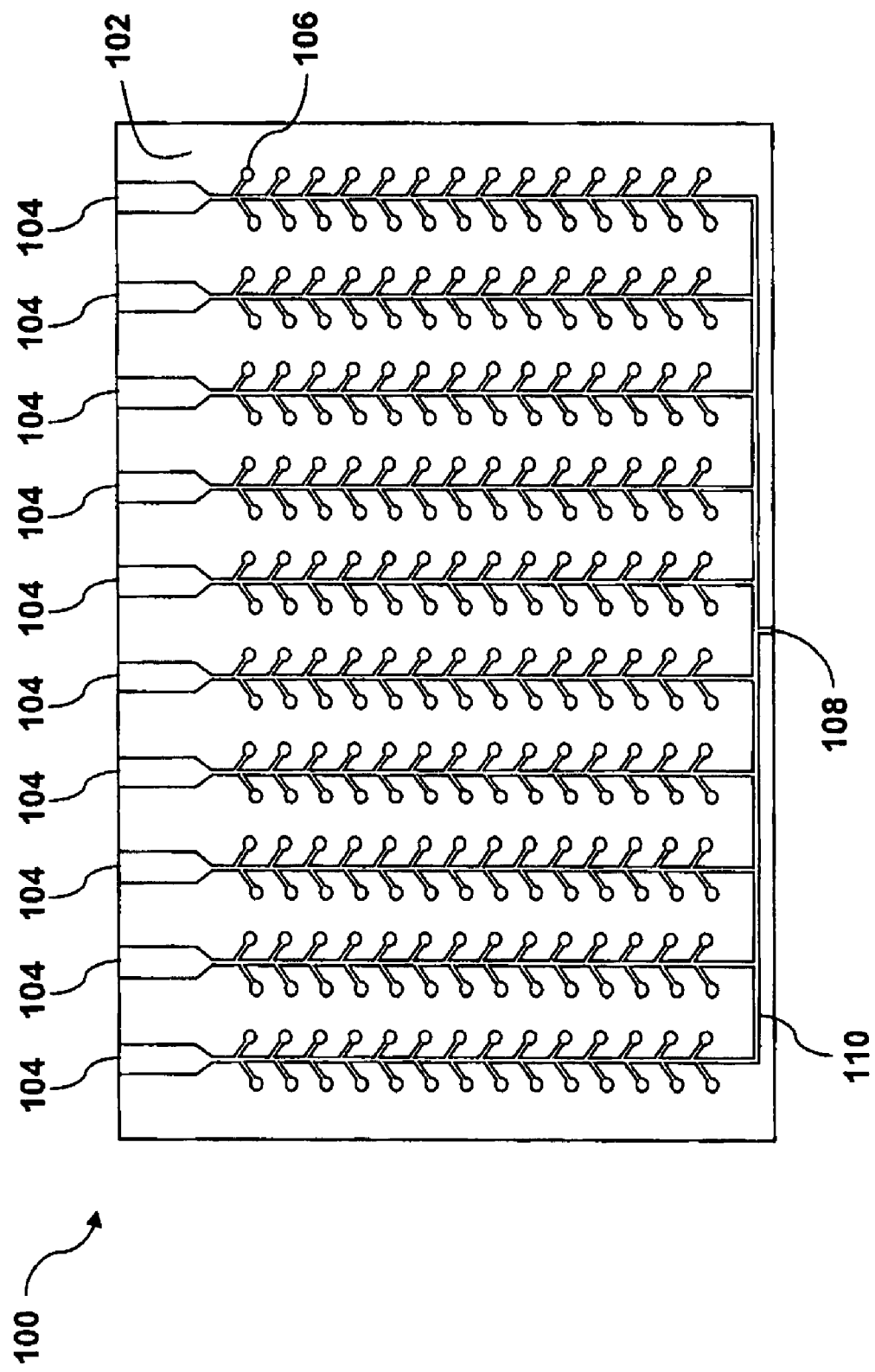
FIG. 1 is a top view of a microfluidic card.

This document provides systems, devices, and methods involved in generating detectable polymers. For example, this document provides diagnostic systems, diagnostic devices, primer systems, and collections of primer systems. A diagnostic system can include a diagnostic device containing primer systems.

In general, a diagnostic device provided herein can include a housing having a plurality of locations. The housing can be any shape and size and can be made from any type of material including, without limitation, plastic, glass, silicone, or metal. For example, a housing provided herein can be rectangular, square, circular, or oval in shape, and can have a length, width, or diameter between five cm and 50 cm (e.g., between ten cm and 40 cm, between ten cm and 30 cm, or between ten cm and 25 cm). The depth or height of a housing provided herein can be between 0.2 cm and 2 cm (e.g., between 0.2 and 1 cm, between 0.3 and 1 cm, or between 0.5 and 1 cm). Each location of a housing can be configured to allow an amplification reaction to occur without primer system contamination from other locations. The locations of a housing provided herein can be any shape or size. For example, the locations of a housing provided herein can be in the configuration of a well or chamber with, for example, the ability to hold a volume between 1 µL and 100 µL (e.g., between 1 µL and 20 µL, between 1 µL and 10 µL, between 1 µL and 5 µL, between 10 µL and 50 µL, or between 15 µL and 25 µL). Such a volume can be 1.5 µL, 10 µL, 20 µL, or 30 µL.

In some cases, a housing can be a 96-well plate with each location being a well of the 96-well plate. A diagnostic device can be in the form of a microfluidic card. Such a card can have a series of locations and channels. The channels can provide fluid communication between a sample inlet port and one or more locations. For example, a housing can be a mircofluidic card having one or more sample inlet ports in fluid communication with one or more locations via one or more channels. In some cases, such a housing can include one or more outlet ports for providing an outlet for added solutions or for providing an outlet for air so that fluid can flow through the channels. In one embodiment, a diagnostic device provided herein can be in the form of a microfluidic card with eight sample inlet ports each connected through channels (e.g., microcapillaries) to 48 locations (e.g., reaction chambers). Another example of a microfluidic card design is depicted in FIG. 1.

With reference to FIG. 1, microfluidic card 100 can have housing 102 defining a plurality of locations 106. While 280 separate locations are shown in this example, a housing provided herein can define any number of locations (e.g., 10, 25, 48, 96, 384, 1536, or more locations). Each location 106 can be in fluid communication with a sample inlet port 104 and an outlet port 108 via channel 110. Any number of channels can be defined by housing 102. For example, a housing provided herein can define one continuous, interconnected channel or can contain multiple separate channels.

A diagnostic device provided herein can contain a collection of primer systems and primer pairs. For example, each primer system or primer pair of a collection can be located at a different location defined by a housing so as to isolate each primer system or primer pair from other primer systems or primer pairs of a collection. For example, each primer system or primer pair of a collection can be housed within a separate location (e.g., a separate well of a plastic microtiter plate or a separate chamber of a microfluidic card). In some cases, each primer system or primer pair of a collection, or a subset of primer systems or primer pair of a collection, can be housed together. For example, one primer system provided herein and one primer pair of a collection of 50 primer systems and primer pairs can be housed within a single well of a plastic microtiter plate with the remaining 48 primer systems and primer pairs being housed within separate wells. In some cases, a system or diagnostic device provided herein can contain at least one primer system set forth in Table 1 (e.g., at least two primer systems set forth in Table 1). In addition to containing any one or more of the primer systems set forth in Table 1 in any combination, a diagnostic device can contain primer systems not listed in Table 1. For example, a diagnostic device can contain a primer system similar to primer system number 1 with the exception that each nucleic acid primer is two nucleotides shorter than those of primer system number 1. In some cases, a diagnostic device can contain a primer pair designed to amplify host nucleic acid (e.g., human genomic nucleic acid or mRNA).

TABLE 1

Optimal primer systems for respiratory syncytial viruses.

| Primer System No. | Primer Sequence | SEQ ID NO: | Length | Tm | Hits* |
|---|---|---|---|---|---|
| 1 | AAAAACACAACAACAACCCAAATAC | 1 | 25 | 60.3 | |
| | TTGAACACTTCAAAGTGAAAATCAT | 2 | 25 | 59.1 | 330 |
| 2 | AAAAACACAACAACAACCCAAATAC | 1 | 25 | 60.3 | |
| | CAAAGTTGAACACTTCAAAGTGAAA | 3 | 25 | 59.8 | 321 |

TABLE 1-continued

Optimal primer systems for respiratory syncytial viruses.

| Primer System No. | Primer Sequence | SEQ ID NO: | Length | Tm | Hits* |
|---|---|---|---|---|---|
| 3 | AAAAACACAACAACAACCCAAATA | 4 | 24 | 59.6 | |
| | CAAAGTTGAACACTTCAAAGTGAAA | 3 | 25 | 59.8 | 320 |

*total number of different gi numbers that is available in Gen-Bank with nucleic acid sequences aligning with each primer of the indicated primer system.

The term "primer system" as used herein refers to a combination of two nucleic acid primers having the ability to amplify nucleic acid provided that the sequence of each nucleic acid primer is from 15 to 50 nucleotides in length and is such that it aligns without a mismatch to a sequence, or its complement, set forth in a GenBank gi number listed in Table 2. For example, each primer of a primer system provided herein can be from 15 to 45 nucleotides the length. In some cases, each primer of a primer system provided herein can range from 20 to 40 nucleotides (e.g., from 20 to 35 nucleotides, from 20 to 30 nucleotides, or from 21 to 28 nucleotides). The primer systems provided herein can be selected such that the length of amplified target nucleic acid, if present within an amplification reaction, would be between 100 and 400 nucleotides (e.g., between 150 and 350 nucleotides, between 175 and 325 nucleotides, or between 200 and 300 nucleotides). The theoretical melting temperature of each primer of a primer system provided herein can be between 58° C. and 62° C. (e.g., between 59° C. and 61° C.). A primer's theoretical melting temperature is calculated as follows:

$$Tm=81.5+16.6(\log10([Na+]))+0.41*(\%GC)-600/\text{length}$$

where [Na+] is 0.005 M. Each primer system provided herein can be used to amplify nucleic acid present in an respiratory syncytial virus.

TABLE 2

| Representative gi numbers for each primer system. | |
|---|---|
| Primer System No. | gi number |
| 1 | 37790367 (SEQ ID NO:5); 45386490 (SEQ ID NO:6); 37790483 (SEQ ID NO:7); 485873 (SEQ ID NO:8); 21929777 (SEQ ID NO:9); 52352480 (SEQ ID NO:10); 21929881 (SEQ ID NO:11); 21929779 (SEQ ID NO:12); 52352474 (SEQ ID NO:13); 37790463 (SEQ ID NO:14); 37790583 (SEQ ID NO:15); 21929761 (SEQ ID NO:16); and 61373253 (SEQ ID NO:17) |
| 2 | 37790367 (SEQ ID NO:5); 45386490 (SEQ ID NO:6); 37790487 (SEQ ID NO:18); 485873 (SEQ ID NO:8); 21929777 (SEQ ID NO:9); 52352480 (SEQ ID NO:10); 21689580 (SEQ ID NO:19); 21929881 (SEQ ID NO:11); 21729393 (SEQ ID NO:20); 37790463 (SEQ ID NO:14); 37790583 (SEQ ID NO:15); 21929779 (SEQ ID NO:12); 21929761 (SEQ ID NO:16); and 61373253 (SEQ ID NO:17) |
| 3 | 37790367 (SEQ ID NO:5); 45386490 (SEQ ID NO:6); 37790487 (SEQ ID NO:18); 485873 (SEQ ID NO:8); 21929777 (SEQ ID NO:9); 52352480 (SEQ ID NO:10) 21929881 (SEQ ID NO:11); 37790463 (SEQ ID NO:14); 37790583 (SEQ ID NO:15); 21929779 (SEQ ID NO:12); 21929761 (SEQ ID NO:16); and 61373253 (SEQ ID NO:17) |

The primer systems provided herein can share unifying advantageous features. For example, each primer system provided herein can amplify nucleic acid from respiratory syncytial viruses. In addition, primer systems provided herein can be selected such that the length of amplified viral nucleic acid would be between 100 and 400 nucleotides. Moreover, the theoretical melting temperature of the primer systems provided herein can be uniformly between 58° C. and 62° C., and the length of each primer of the primer systems provided herein can range from 15 to 50 nucleotides (e.g., from 21 to 28 nucleotides). These unifying characteristics can contribute to the effective detection of nucleic acid from respiratory syncytial viruses present within samples.

The primer systems listed in Table 1 can be used effectively to detect a large group of different respiratory syncytial viruses. For example, primer system number 1 can have the ability to detect respiratory syncytial virus nucleic acid sequences associated with 330 different GenBank gi numbers.

Any method can be used to make the primers of a primer system provided herein. For example, chemical synthesis techniques such as those described elsewhere (Beaucage and Caruthers, *Tetrahedron Lett.,* 22:1859-62 (1981)) can be used. In addition, nucleic acid primers can be obtained from commercial vendors such as MWG Biotech, Invitrogen, and Operon.

Any method can be use to make a system or diagnostic device provided herein. For example, a diagnostic device provided herein can be made as follows. A 384-well master plate containing 125 μL of one or more primer systems in dioinized water at a working concentration of 100 nmole/1 μL of each primer can be constructed. The master plate can be used as a template source, and 1 μL of each master plate well can be transferred to corresponding wells on a 384-well microfluidic card. Spotted reagents can be allowed to dry at room temperature before the final plastic laminate layer of the microfluidic card is attached.

The primer systems provided herein can be used separately or in combinations with other primer systems provided in Table 1 or other primer pairs. When making a combination, any two or more primer pairs or primer systems provided herein can be arranged into any combination.

The diagnostic devices and primer systems provided herein can be used to detect respiratory syncytial viruses present within samples. For example, a sample can be obtained from a human (or other animal such as a bird) and used in an amplification reaction to determine whether or not an respiratory syncytial virus' nucleic acid is present in the sample. Any type of sample can be used including, without limitation, a biopsy (e.g., punch biopsy, aspiration biopsy, excision biopsy, needle biopsy, or shave biopsy), a tissue section, lymph fluid, mucus, blood, serum, and saliva samples. A sample can be obtained from a human or any other animal suspected to contain an respiratory syncytial virus (e.g., birds, pigs, and horses). In some cases, a sample can be obtained from a mammal (e.g., a human) using a swab (e.g., an OmniSwab; Whatman). The presence of an amplification product following an amplification reaction using, for example, a human's mucus sample and a primer system provided herein can indicate that that sample contains an respiratory syncytial virus. In such a case, the human can be diagnosed as being infected with an respiratory syncytial virus.

Some sample types can be pre-processed to enhance sample quality. For example, a mucus sample can be treated with a mucolytic agent to liquefy mucus within a mucus sample. Samples can be processed to concentrate the nucleic acid and render it in a form to facilitate successful PCR reactions. This includes, but is not limited to, common methods to disrupt bilipid membranes, such as the use of detergents, digestion of protein complexes, such as the use of proteinase K, and reduction of polymerase inhibitors through the use of selective affinity columns. Commercial kits for purification of DNA, RNA, or total nucleic acid are readily available from, for example, Qiagen and Roche. In some cases, a sample can be processed using a Qiagen QIAmp Viral RNA Mini Kit.

Any type of amplification reaction can be used in conjunction with the primer systems set forth in Table 1 to detect respiratory syncytial viruses. For example, common PCR reactions designed to amplify nucleic acid from DNA or RNA can be used. Detection of RNA viruses can be accomplished by synthesizing cDNA from RNA sequence templates. cDNA synthesis can be accomplished using standard methods using, for example, RNA-dependant DNA polymerases, such as reverse transcriptase. Such reactions can be primed with random oligonucleotide sequences, such as random hexamers and octamers, or by sequence specific oligonucleotide primers, including the same primers used for the PCR reaction. The cDNA synthesis can be performed in a separate reaction vessel from the subsequent PCR reaction (commonly referred to as two-step rtPCR) or in the same reaction vessel as the PCR reaction (commonly referred to as single-step rtPCR).

Purified DNA and cDNA samples can be pooled and added to a PCR master mix containing water, salt buffers, magnesium ions, nucleotide monomers (dATP, dCTP, dGTP and dTTP), native or engineered *Thermus aquaticus* DNA-dependant DNA polymerase, and an intercalating dye, such as Sybr Green or LC Green. The master mix and sample can then be added to a single loading port of a microfluidic card and dispersed to all the reaction wells using centrifugation. The cards can then be scored to isolate and seal each reaction chamber prior to thermocycling. The cards can be individually thermocycled using commodity block thermocyclers or many cards thermocycled simultaneously using air- or water-based thermocyclers such as the BioOven or the H2OBIT, respectively.

Positive PCR amplification reactions can be detected during thermocycling for quantitative or qualitative analysis (real time PCR) or after completion of thermocycling (qualitative end-point PCR). Signals can be detected through fluorescence-channel emission of substrate bound intercalating dyes using commodity real-time PCR capable PCR platforms or by end-point reads using microplate scanner platforms. Both types of platforms can be used for melting-point analysis for validation of positive signals.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device comprising a housing having a plurality of locations, wherein at least one of said locations comprises any one of Primer Systems 1, 2, or 3 of Table 1.

2. The device of claim 1, wherein each of said locations is a chamber.

3. The device of claim 1, wherein each of said locations is a well.

4. The device of claim 1, wherein at least one of said locations comprises a different primer pair.

5. The device of claim 4, wherein said different primer pair capable of producing an amplification product from human nucleic acid.

6. The device of claim 1, wherein each of said locations comprises an intercalating dye.

7. The device of claim 6, wherein said intercalating dye is a green fluorescent dye.

8. The device of claim 6, wherein said intercalating dye is SYBR Green, LC Green, or SYTO9.

9. A method for detecting a respiratory syncytial virus within a sample, wherein said method comprises:
    (a) performing a nucleic acid amplification reaction using said sample as a source of template and a diagnostic device, wherein said device comprises a housing having a plurality of locations, wherein at least one of said locations contains any one of Primer Systems 1, 2, or 3 of Table 1, and
    (b) determining whether or not the location containing said primer system comprises said amplification product, thereby detecting a respiratory syncytial virus.

10. The method of claim 9, wherein said sample is a mucus sample obtained from a human.

11. The method of claim 9, wherein each of said locations comprises an intercalating dye, wherein each amplification product, when produced, is labeled with said intercalating dye, and wherein said determining step (b) comprises a signal from said dye.

12. The method of claim 9, wherein said amplification reaction is performed in a thermal cycler device configured to receive said diagnostic device.

13. The method of claim 9, wherein said determining step (b) is performed using a dye reader device configured to receive said diagnostic device.

14. The method of claim 9, wherein said amplification reaction and said determining step (b) are performed in a machine configured to receive said diagnostic device, said machine comprising a thermal cycler device and a dye reader device.

15. The method of claim 14, wherein said machine is capable of providing output indicating the presence of said respiratory syncytial virus.

16. The method of claim 14, wherein said machine is capable of providing output identifying indicating the primer system that detected the presence of said respiratory syncytial virus.

17. The method of claim 16, wherein said output is a paper printout or a computer readable file.

* * * * *

UNITED STATES PATENT AND TRADEMARK OFFICE
CERTIFICATE OF CORRECTION

PATENT NO. : 7,521,189 B2
APPLICATION NO. : 11/549008
DATED : April 21, 2009
INVENTOR(S) : Eric Engelhard Page 1 of 1

It is certified that error appears in the above-identified patent and that said Letters Patent is hereby corrected as shown below:

Title Page, Item (56) References Cited, Other Publications, Mazzulli et al. reference, please delete "Repiratory" and insert --Respiratory-- therefor;

Column 28, line 9 (Claim 16), before "indicating" please delete "identifying".

Signed and Sealed this

Eighteenth Day of August, 2009

David J. Kappos
*Director of the United States Patent and Trademark Office*